(12) United States Patent
Schwammberger et al.

(10) Patent No.: US 7,731,718 B2
(45) Date of Patent: Jun. 8, 2010

(54) IMPLANT FOR THE TREATMENT OF BONE FRACTURES

(75) Inventors: Andy Schwammberger, Hölstein (CH); Jordan Velikov, Thalwil (CH)

(73) Assignee: Zimmer, GmbH, Winterthur (CH)

( * ) Notice: Subject to any disclaimer, the term of this patent is extended or adjusted under 35 U.S.C. 154(b) by 25 days.

(21) Appl. No.: 10/814,926

(22) Filed: Mar. 31, 2004

(65) Prior Publication Data

US 2004/0225291 A1 Nov. 11, 2004

(51) Int. Cl.
*A61B 17/80* (2006.01)
(52) U.S. Cl. .................................................. 606/71
(58) Field of Classification Search .............. 606/60, 606/65–71, 74, 86, 281–286, 86 R
See application file for complete search history.

(56) References Cited

U.S. PATENT DOCUMENTS

| | | | |
|---|---|---|---|
| 3,386,799 A | 6/1968 | Grodkiewicz et al. | |
| 1,118,773 A | 7/1968 | Hammond et al. | |
| 3,561,437 A | 2/1971 | Orlich | |
| 3,604,414 A | 9/1971 | Borges | |
| 3,741,205 A | 6/1973 | Markolf et al. | |
| 3,807,394 A | 4/1974 | Attenborough | |
| 3,814,089 A | 6/1974 | Deyerle | |
| 4,096,857 A | 6/1978 | Cramer et al. | |
| 4,465,065 A | 8/1984 | Gotfried | |
| 4,957,496 A | 9/1990 | Schmidt | |
| 5,006,120 A | 4/1991 | Carter | |
| 5,066,296 A | 11/1991 | Chapman et al. | |
| 5,376,126 A * | 12/1994 | Lin .......................... | 623/23.11 |
| 5,665,089 A | 9/1997 | Dall et al. | |
| 5,797,916 A | 8/1998 | McDowell | |
| 5,993,452 A * | 11/1999 | Vandewalle .............. | 606/74 |
| 6,066,141 A * | 5/2000 | Dall et al. ................ | 606/74 |
| 6,123,709 A * | 9/2000 | Jones ........................ | 606/69 |
| 6,348,052 B1 | 2/2002 | Sammarco | |
| 6,514,274 B1 * | 2/2003 | Boucher et al. ........... | 606/232 |
| 6,520,965 B2 * | 2/2003 | Chervitz et al. .......... | 606/74 |
| 6,576,018 B1 * | 6/2003 | Holt ......................... | 623/21.11 |
| 6,932,820 B2 * | 8/2005 | Osman ..................... | 606/71 |
| 7,207,993 B1 * | 4/2007 | Baldwin et al. .......... | 606/70 |
| 7,335,204 B2 | 2/2008 | Tornier | |
| 2001/0051815 A1 * | 12/2001 | Esplin ..................... | 606/232 |
| 2002/0062127 A1 | 5/2002 | Schumacher et al. | |
| 2002/0128654 A1 * | 9/2002 | Steger et al. ............. | 606/69 |
| 2002/0143336 A1 * | 10/2002 | Hearn ...................... | 606/69 |
| 2002/0183753 A1 | 12/2002 | Manderson | |
| 2003/0130661 A1 * | 7/2003 | Osman ..................... | 606/71 |
| 2004/0087954 A1 * | 5/2004 | Allen et al. .............. | 606/74 |

(Continued)

FOREIGN PATENT DOCUMENTS

CA 2047521 1/1992

(Continued)

*Primary Examiner*—Thomas C Barrett
*Assistant Examiner*—Michael J Araj
(74) *Attorney, Agent, or Firm*—Baker & Daniels LLP

(57) ABSTRACT

The invention relates to an implant for the treatment of bone fractures, in particular of proximal humerus fractures, having a main plate which can be fixed to the bone and at least one outrigger which can be connected to the main plate via at least one flexible connection element such that the outrigger can be fixed to the bone spatially offset with respect to the main plate.

26 Claims, 10 Drawing Sheets

U.S. PATENT DOCUMENTS

Figure 1:
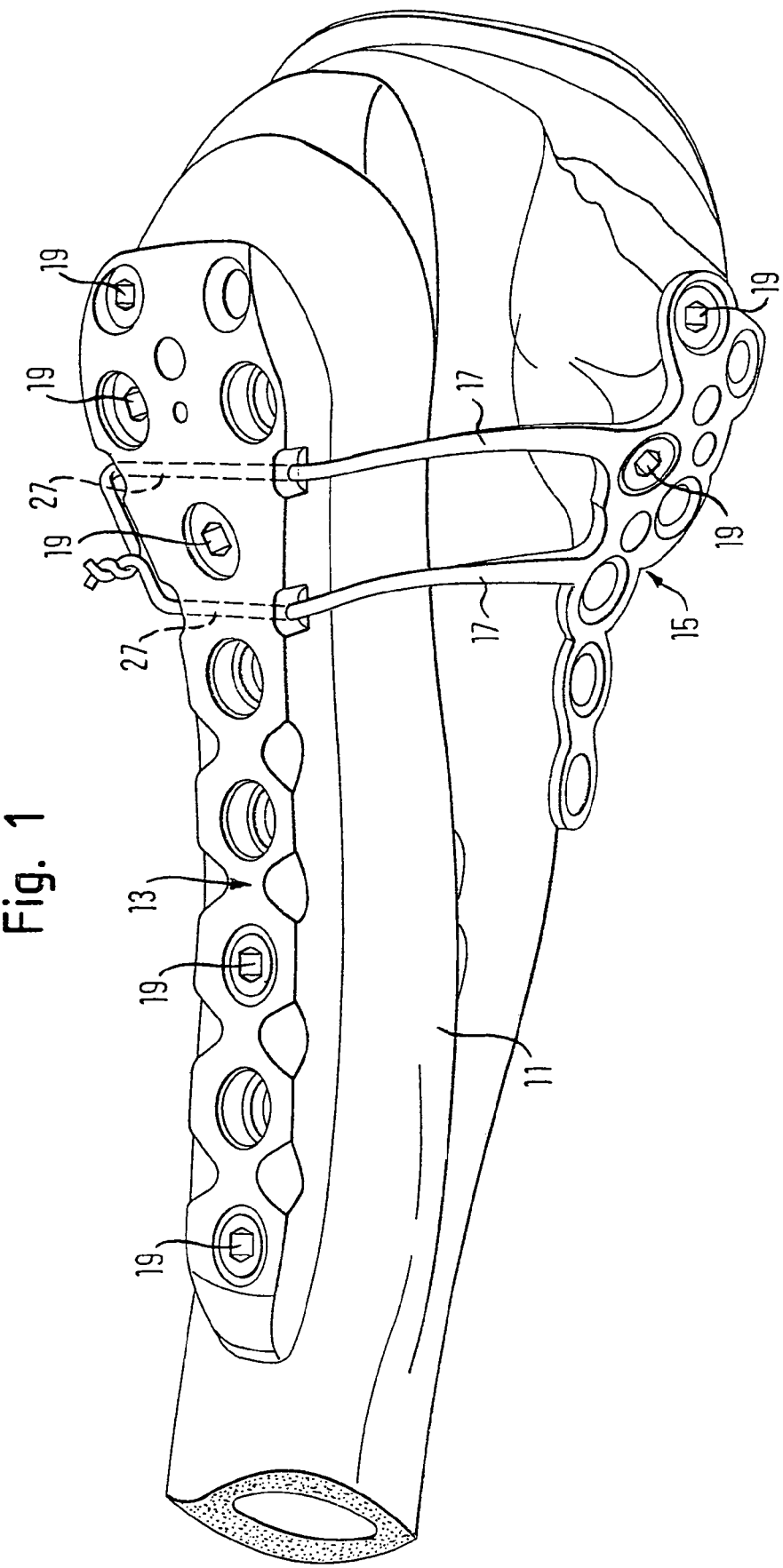

| | | |
|---|---|---|
| 2004/0097937 A1 | 5/2004 | Pike et al. |
| 2004/0116930 A1 | 6/2004 | O'Driscoll et al. |
| 2004/0116931 A1 * | 6/2004 | Carlson .................. 606/70 |

FOREIGN PATENT DOCUMENTS

| | | |
|---|---|---|
| DE | 27 05 154 A1 | 8/1978 |
| DE | 102 26 074 A1 | 1/2003 |
| DE | 10226074 A1 | 1/2003 |
| EP | 0 491 382 B1 | 8/1996 |
| EP | 0 468 192 B1 | 9/1996 |
| EP | 0 791 338 A2 | 8/1997 |
| EP | 0 897 233 A2 | 2/1999 |
| FR | 2 291 734 | 6/1976 |
| FR | 2 827 500 A1 | 1/2003 |
| FR | 2827500 A1 | 1/2003 |
| JP | 10-179605 A | 7/1998 |
| JP | 3388741 B2 | 1/2003 |
| WO | WO 89/09037 | 10/1989 |
| WO | WO03032849 A1 * | 4/2003 |

* cited by examiner

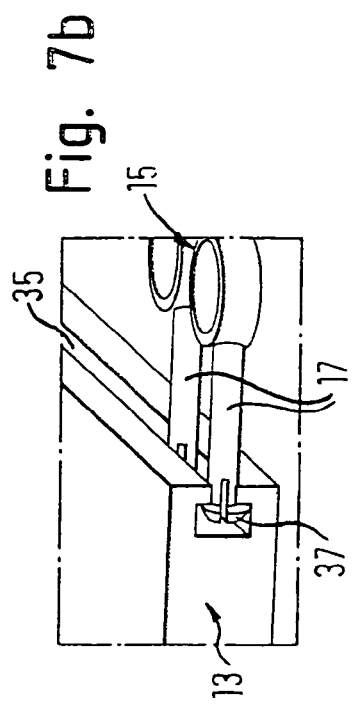
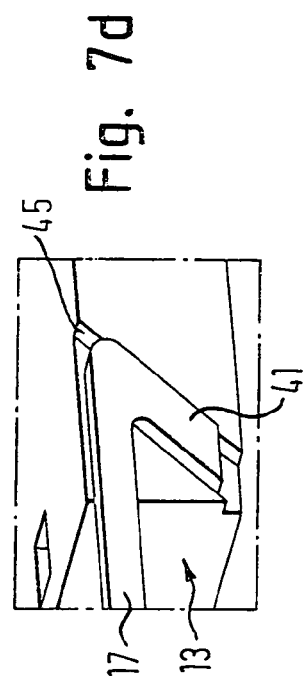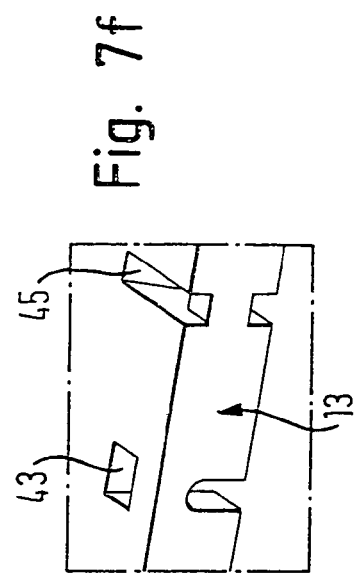
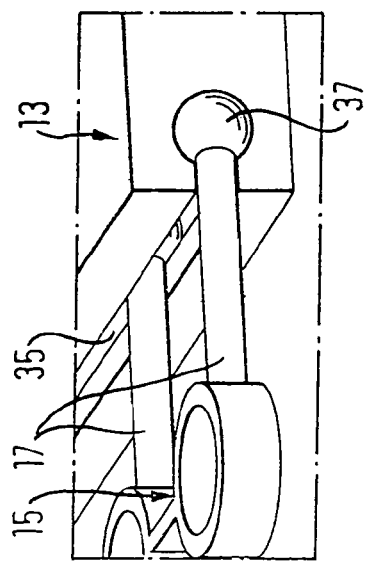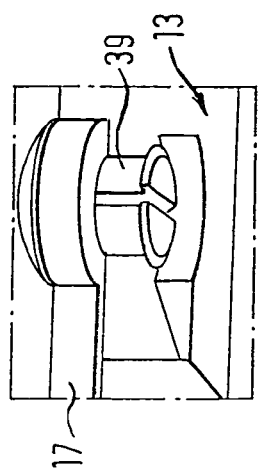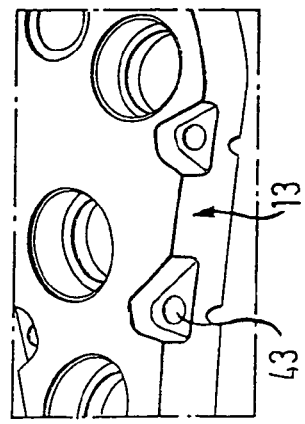

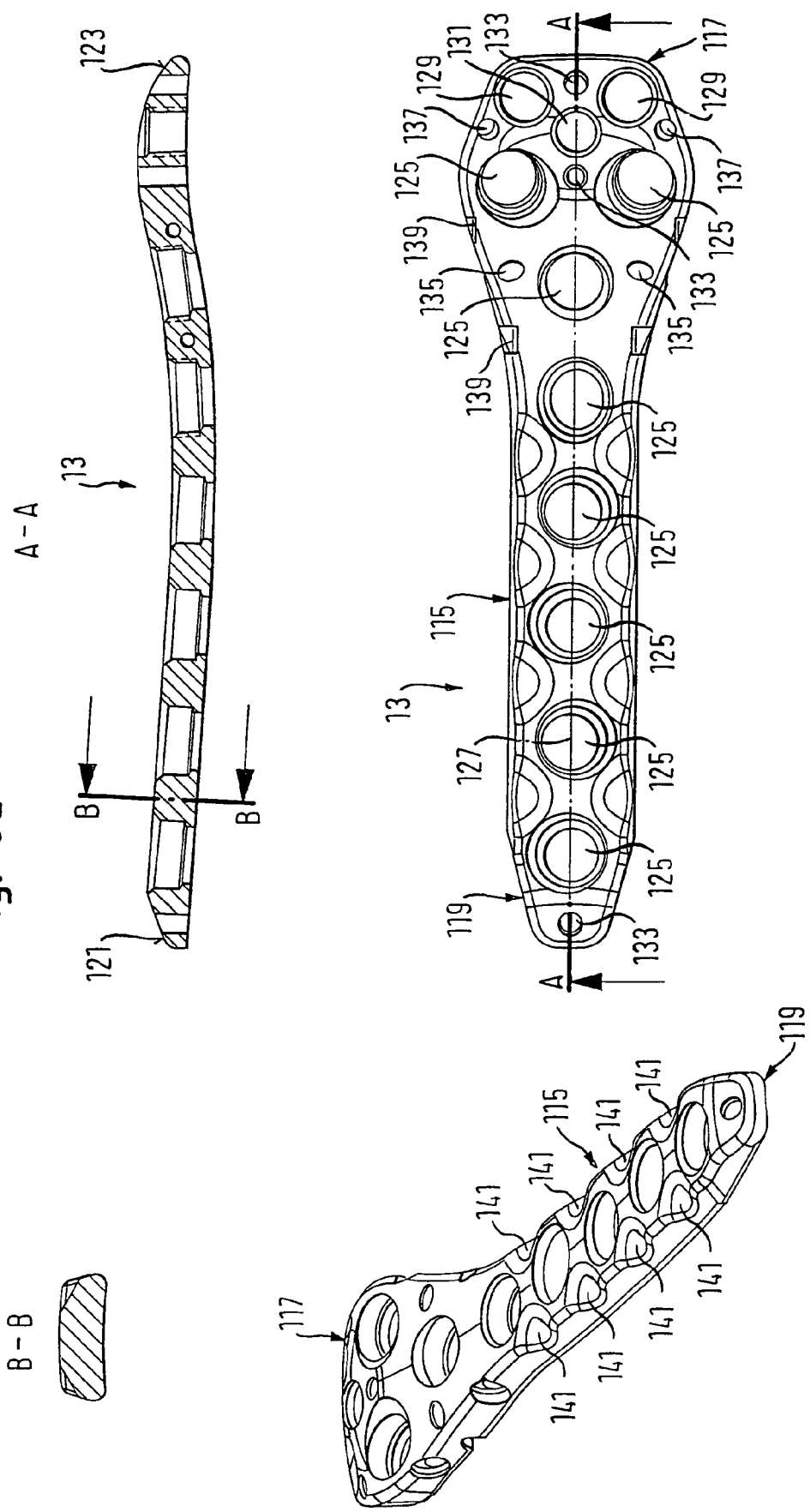

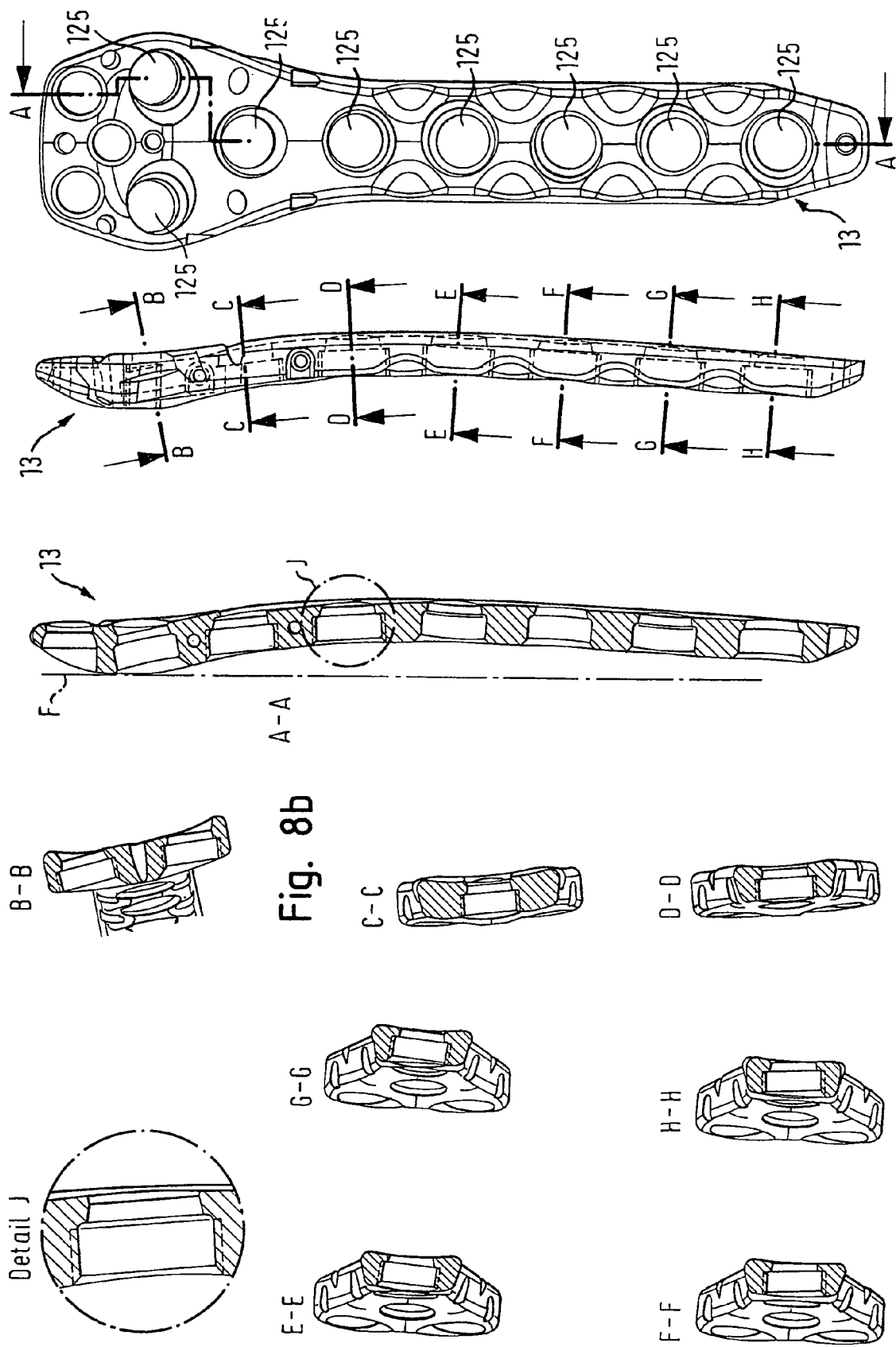

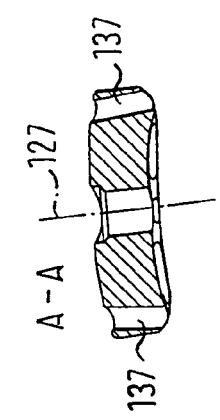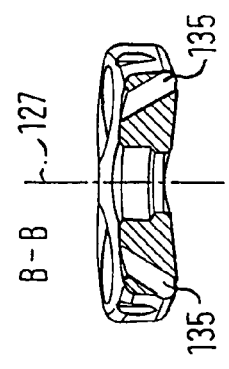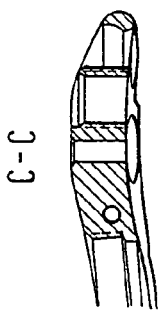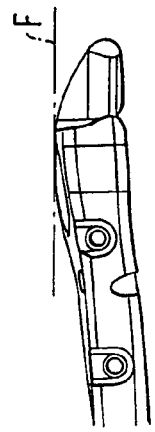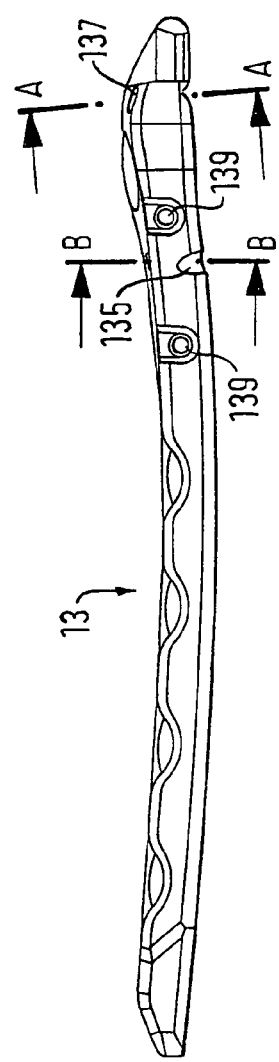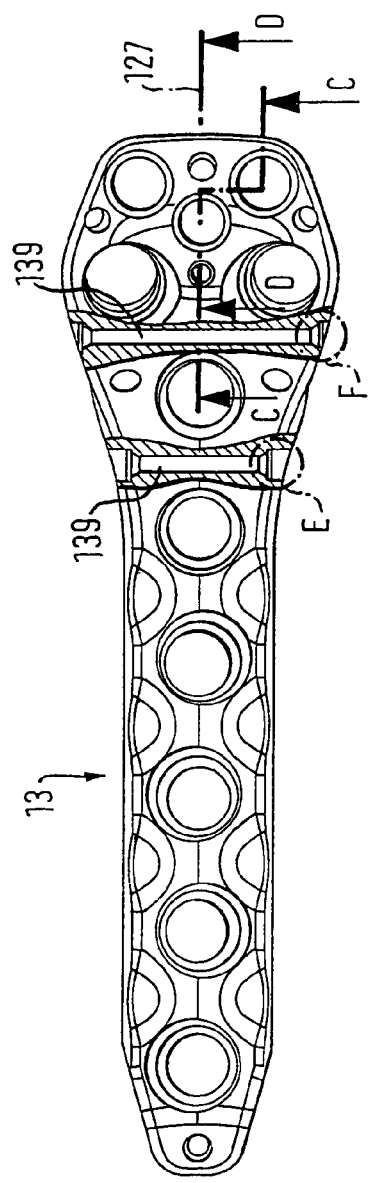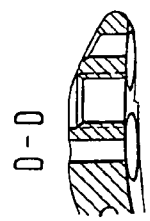
Fig. 8c

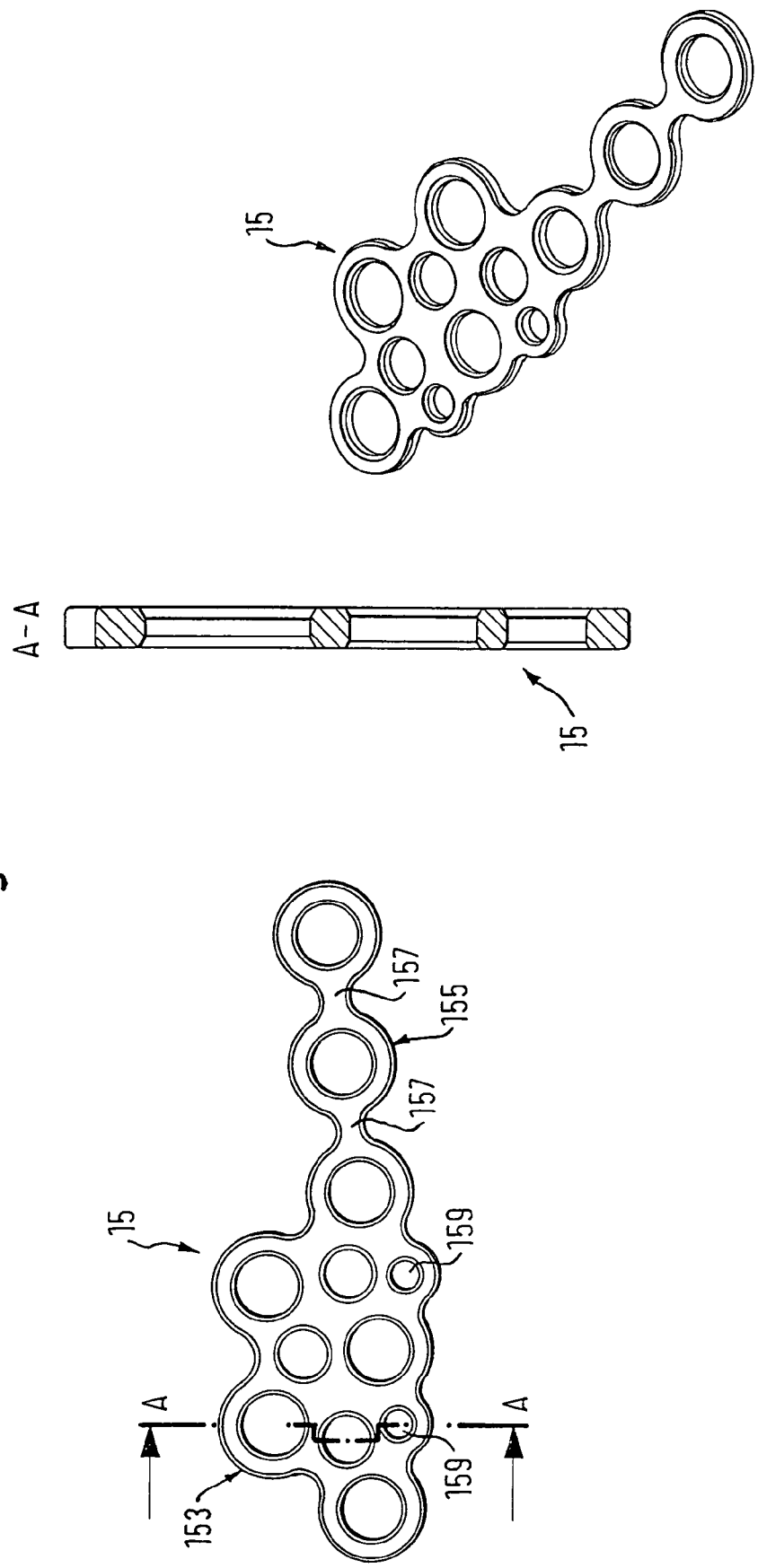

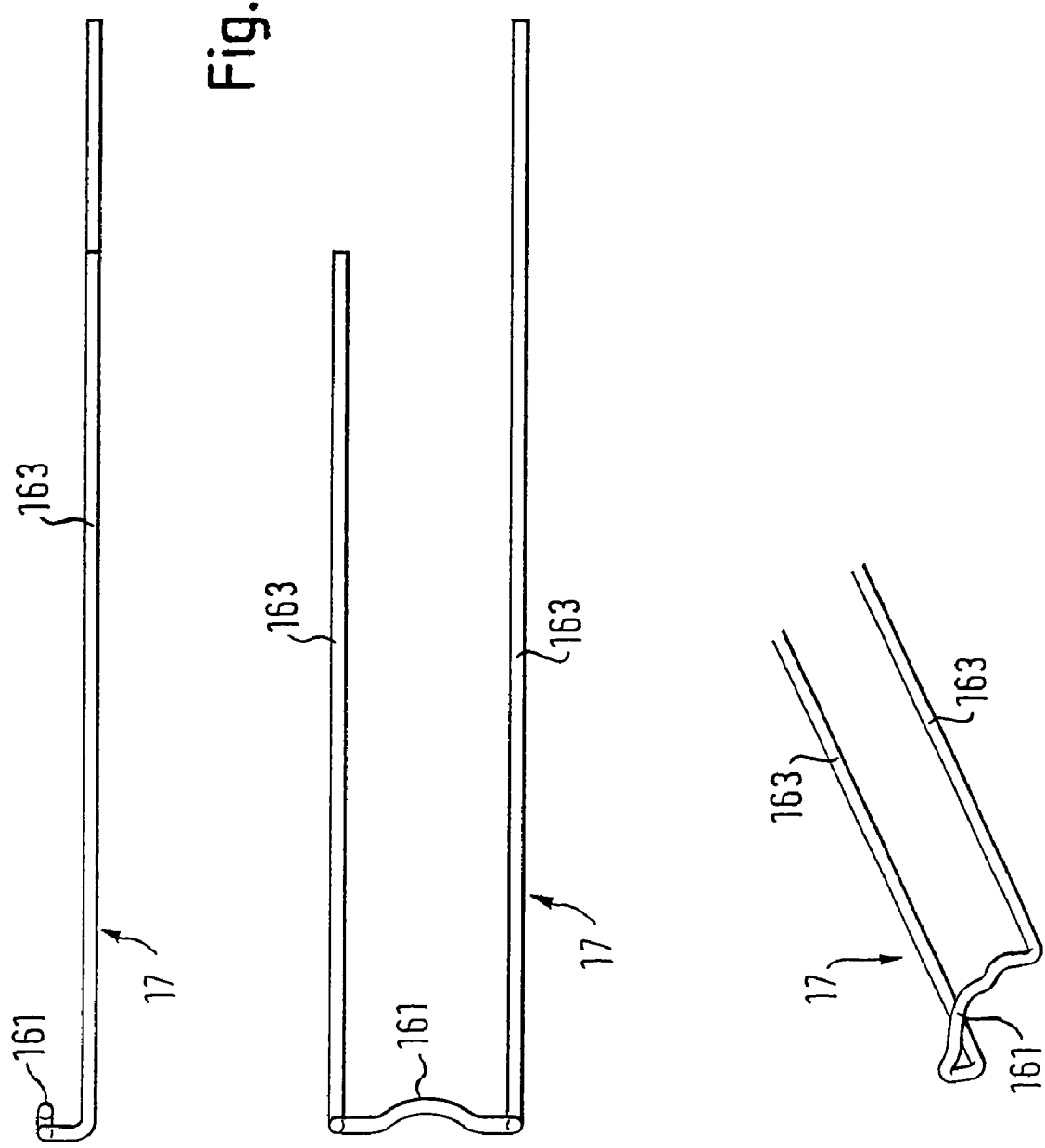

IMPLANT FOR THE TREATMENT OF BONE FRACTURES

CROSS REFERENCE TO RELATED APPLICATION

This application claims priority of European Patent Application Numbers 03 007 543.6 filed Apr. 1, 2003 and 04 002 710.4 filed Feb. 6, 2004.

The invention relates to an implant for the treatment of bone fractures with a main plate which can be fixed to the bone.

Such implants, which are also known as osteosynthetic plates, serve, for example, for the treatment of proximal humerus fractures and are generally known, for example from EP 0 468 192 B1.

Certain fractures, in particular such with a plurality of individual bone fragments or such at the humerus, in which the tuberculum minus is also affected, cannot be ideally treated with such plates. In particular such cases are problematic in which regions of the bone which lie comparatively far apart are also affected by the fracture.

It is the object of the invention to provide a possibility, starting from an implant of the kind first mentioned, of caring for the most varied fractures safely and reliably, with it in particular also being possible to treat complicated and comparatively extended fractures satisfactorily.

This object is satisfied by the features of claim 1 and in particular in that the implant includes a main plate which can be fixed to the bone and at least one outrigger which can be connected to the main plate via at least one flexible connection element such that the outrigger can be fixed to the bone in a manner spatially offset to the main plate.

Generally, any desired spatial implant structures can be realised with the implant in accordance with the invention and can be fixed to the bone to be treated in a configuration directly matched to the respective fracture. The implant can be placed around the bone or at the bone like a stabilisation cage or a holding cage encompassing the affected region or like a holding clamp or stabilisation clamp surrounding the affected region. The flexibility of the connection element allows an optimum matching both to the shape of the bone and to the course of the respective fracture. The implant in accordance with the invention can achieve a very exact resetting of the individual bone fragments overall and give the fracture optimum stability with the outrigger which can be fixed to the bone in a manner offset peripherally with respect to the main plate.

Advantageous embodiments of the invention are recited in the dependent claims, in the description and in the drawing.

In a preferred embodiment of the invention, the outrigger is formed in a plate shape.

Provision can furthermore be made for the outrigger to be made flexibly and in particular to be able to be brought into a respectively required spatial shape by bending. The position of the outrigger cannot only hereby be directly chosen relative to the main plate due to the flexibly designed connection element, but the outrigger can additionally be matched to the anatomy of the bone.

Furthermore, it is proposed in accordance with the invention for the outrigger to be able to be cut to the respectively required shape and size. This matching capability of the shape and size of the outrigger to the respective circumstances makes it possible to provide a tailored implant for the respective fracture.

The outrigger can have a plurality of passages for the reception of fastening elements. In particular bone screws can be considered as fastening elements. The fastening of the outrigger to the bone can therefore generally take place in the same manner as the fixing of the main plate.

The outrigger can in particular be provided in the form of a perforated plate.

In a further embodiment of the invention, the outrigger is made in mesh-like or grid-like form. With such a mesh-like or grid-like structure of the outrigger, a plurality of passages or openings are available in the outrigger through which fastening elements, in particular bone screws, serving for the fixing of the outrigger to the bone can be guided. The outrigger in accordance with the invention, and thus the implant in accordance with the invention, can hereby be used in a particularly flexible and versatile manner.

Provision can be made for the outrigger to include a plurality of ring sections connected to one another directly or by webs and each bordering a passage.

The outrigger can be made in one piece with the connection element. Alternatively or additionally, it is possible for the outrigger to be provided, for example, with eyelet-like or ring-like fastening sections which serve for the coupling to the connection element.

In a further preferred embodiment of the invention, provision is made that the spatial offset between the main plate and the outrigger is individually adjustable, and indeed in particular by means of the connection element.

This can in particular be achieved in that the connection element can be fixed to the main plate and/or to the outrigger at different positions.

In an embodiment of the invention, the main plate can have at least one passage for the guiding through of the connection element. The passage can extend substantially parallel to the plate plane defined by the main plate.

The connection element preferably has an elongate shape. Provision can furthermore be made for the connection element to be bendable. The connection element can in particular be a wire or a thread. In accordance with the invention, the connection element can be formable both plastically and elastically.

The coupling of the connection element to the main plate and/or to the outrigger can take place by tying, hooking and/or latching.

The number of individual connection elements between the main plate and the outrigger can generally be any desired one. A number of two connection elements extending approximately parallel to one another has provided to be sufficient both with respect to handling and to precision and stability.

In accordance with the invention, provision can furthermore be made for at least two connection elements guided in each case through at least one passage of the main plate can be connected to one another at the side of the main plate remote from the outrigger. This connection can in particular take place by knotting or twisting the free ends of the connection elements together, with in particular a tensile strength being able to hereby be produced between the outrigger and the main plate.

The outrigger and/or the connection plate are in particular made of metal, e.g. titanium, or of plastic. The plastics can be bio-absorbable plastics such as lactates. If, in such a case, bio-absorbable connection elements, for example bio-absorbable suturing material, are also used, the explanting of the main plate can take place with a minimal invasive operation.

Provision can furthermore be provided for the main plate and/or the outrigger to have at least one hook-like or claw-like continuation. The positioning and fixing of the main plate or of the outrigger to the bone can be facilitated by such a continuation.

Furthermore, provision is preferably made in accordance with the invention for different implant configurations of main plate and of outrigger connected to the main plate to be able to be established which are symmetrical with respect to the main plate and in particular with respect to a longitudinal axis of the main plate. For example, a left/right symmetry of the implant can thus be realised which enlarges its application possibilities.

In accordance with a further embodiment of the invention, provision can be made for the outrigger and the connection element to be manufactured separately and to be connected so firmly to one another that the outrigger and the connection element can be handled as one unit during an operation. The handling of the implant in accordance with the invention is hereby substantially simplified during the operation, with it, however, still being generally possible to set the spatial offset between the main plate and the outrigger individually in that the main plate is moved relative to the connection element before the final fixing of the outrigger to the main plate takes place.

The outrigger and the connection element are preferably unreleasably connected to one another. An intimate connection between the outrigger and the connection element can be established by welding, for example. It is admittedly possible, but not absolutely necessary, for the outrigger and the connection element to be made of the same material. The outrigger can thus, for example be made of plastic and the connection element of metal, or vice versa.

In accordance with a further preferred embodiment of the invention, the main plate and the outrigger are connected to one another at one side via the connection element. Considered from the main plate, for example, the connection element consequently extends only starting from one side of the main plate to the outrigger. The main plate, the outrigger and the connection plate in particular do not form any "closed" structure in the implanted state which surrounds the bone in question around its full periphery, i.e. no "wrapping around" of the bone in question by the implant in accordance with the invention takes place in this embodiment. The bone is rather only "encompassed" by the implant in accordance with the invention over part of its periphery. In this process, the length of the connection element or the spacing between the main plate and the outrigger can be dimensioned in dependence on the bone in question and on the fracture to be treated such that the main plate and the outrigger do not lie diametrically opposite one another at the bone.

It is furthermore proposed in accordance with the invention that the outrigger is formed in plate shape and has a smaller thickness than the main plate. The thickness of the outrigger can in particular amount to less than half the thickness of the main plate.

The outrigger can furthermore be made such that it is deformable without tools during an operation. The surgeon can hereby deform the outrigger directly with his hands, in particular by bending, during the operation such that the outrigger is ideally matched to the contour of the bone while taking its desired position into account.

In an outrigger of bioabsorbable material, for example of a polymer, and in bioabsorbable connection elements in the form of threads, as is provided in a preferred embodiment, the later explantation is superfluous, if bioabsorbable bone screws are also used for anchoring.

Furthermore, bioabsorbable polymers can be provided for the outrigger which permit plastic deformation by hand when they have been heated to temperatures between 50 and 90° C. in a salt bath, for example in Ringer's solution.

It is furthermore proposed that the outrigger has a smaller base area than the main plate.

Provision can furthermore be made in accordance with the invention for the outrigger to have a base shape sufficiently large for all common fractures of a certain bone and to be able to be cut to the required shape and size for matching to a respective bone fracture to be treated.

The outrigger is preferably provided with at least five passages to receive fastening elements, with the fastening elements preferably being provided in the form of bone screws.

The invention moreover relates to an implant system for the treatment of bone fractures, in particular of proximal humerus fractures, having at least one main plate fixable to the bone, at least one outrigger and one set of flexible connection elements, via which the outrigger can be connected to the main plate such that the outrigger can be fixed to the bone spatially offset to the main plate, with the connection elements being prefabricated ready for use and differing from one another with respect to shape, size and/or length.

The surgeon in this process can choose the respectively suitable connection element from a set of prefabricated connection elements during the operation and can put together an implant ideally matched to the respective fracture without any time loss.

A possible fastening to the main plate can consist of the wires or threads coming from the outrigger being fastened to the main plate by crimping.

Provision is preferably made that at least one of the connection elements has a U shape and at least one respective pair of passages, in particular provided in the form of bores, is made for a connection element both in the outrigger and in the main plate and their spacing corresponds to that of the U limbs of the connection element.

A set of outriggers can furthermore be provided in accordance with the invention which differ from one another at least with respect to the number of passages serving for the reception of fastening elements, in particular in the form of bone screws. The outriggers moreover in particular differ from one another with respect to their size and/or shape. A cutting to shape of outriggers having only one single base shape or size can hereby be omitted during the operation.

The implant in accordance with the invention of main plate and outrigger is used in the context of an open operation, i.e. minimum invasive techniques are not used in connection with the implant in accordance with the invention.

Preferably, however, the main plate is made such that it cannot only be used in conjunction with the outrigger in accordance with the invention, but can also be used alone. For the treatment of fractures in which the additional outrigger is not desired or required, the main plate can then also be used in the context of a minimum invasive operation and can be inserted into the body and positioned at the bone via a small incision into the body with the aid of a handle releasably connected to the main plate. For the fixing of the main plate to the bone, the handle is formed as a targeting aid for bone screws or the handle is replaced by such a targeting aid. When the outrigger in accordance with the invention is not used, the main plate can consequently be used as is described in EP 0 468 192 B1 already described initially.

When the implant in accordance with the invention of main plate and outrigger is used, the outrigger can generally be connected to the main plate via the connection element either prior to or after the fixing of the main plate to the bone and can subsequently likewise be fixed to the bone.

Figure 2:
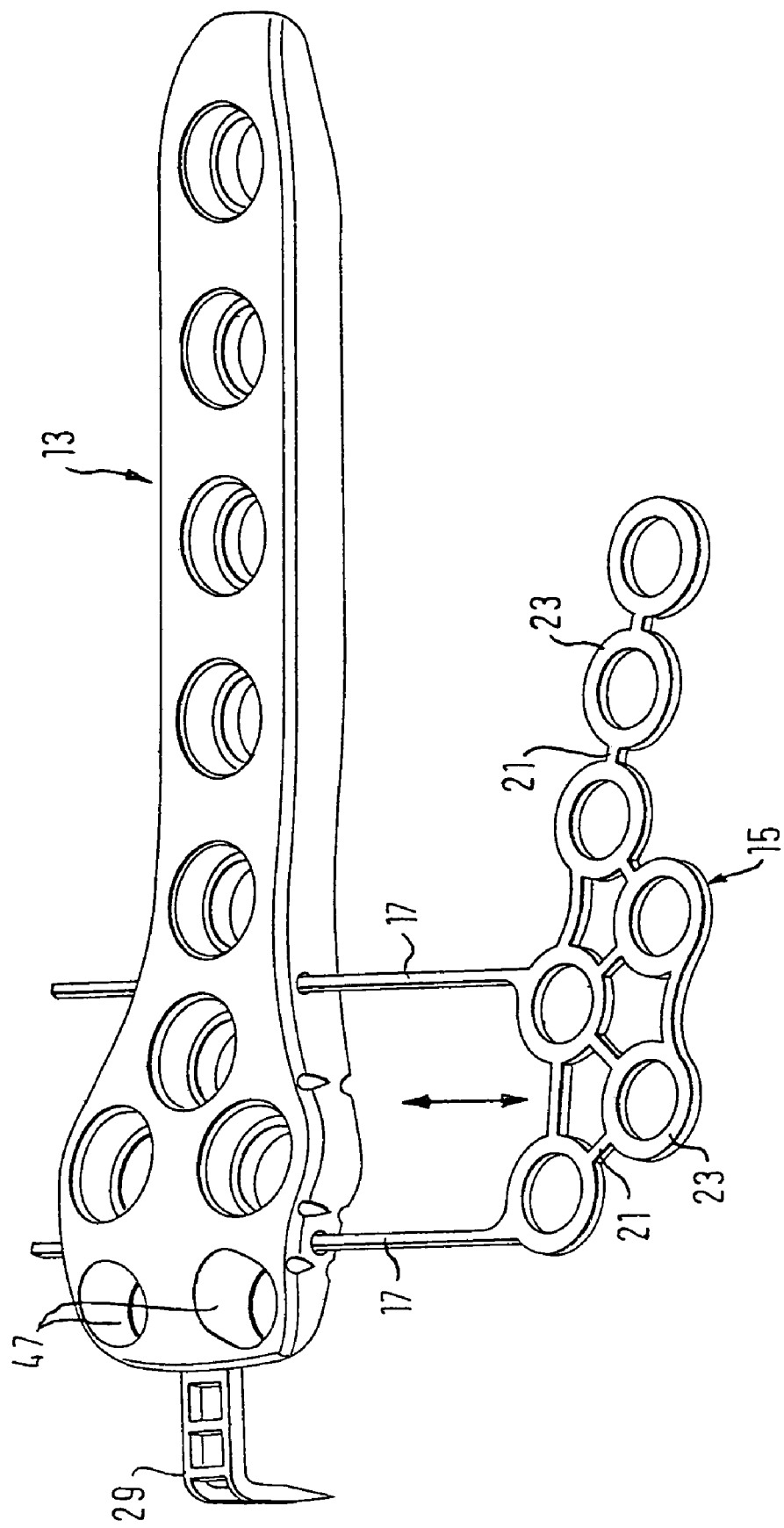
Figure 6:
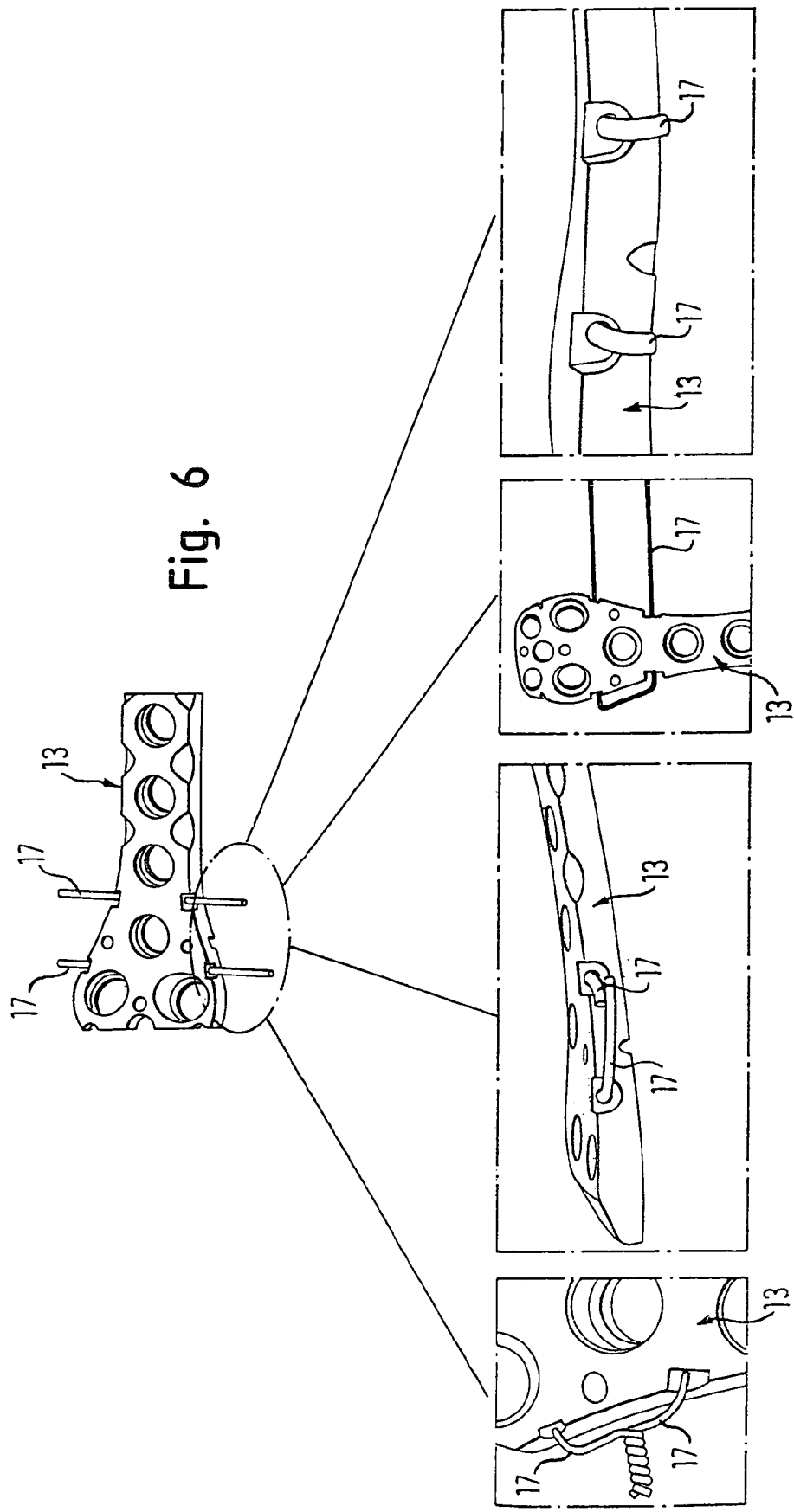

The invention will be described in the following by way of example with reference to the drawings. There are shown:

FIG. 1 an embodiment of an implant in accordance with the invention in a state fixed to the bone;

FIG. 2 a further embodiment of an implant in accordance with the invention;

FIGS. 3, 4, 5a-5c various embodiments of an outrigger of an implant in accordance with the invention;

FIG. 6 different possibilities for the coupling of connection elements to a main plate of an implant in accordance with the invention;

FIGS. 7a-7f further possibilities for the coupling of a connection element to a main plate of an implant in accordance with the invention or specific aspects of the main plate;

FIGS. 8a-8c different views of a main plate in accordance with a further embodiment of the invention;

FIG. 9 different views of an outrigger in accordance with a further embodiment of the invention; and FIG. 10 different views of a connection element in accordance with a further embodiment of the invention.

FIG. 1 shows an implant in accordance with the invention consisting of a main plate 13, of a plate-like outrigger 15 as well as of two connection elements 17 which is used here for the treatment of the humerus 11, with the outrigger 15 serving for the fastening to bone fragments; with the humerus 11, for example, to a tuberculum minus fracture. The outrigger plate 15 does not extend in one plane, but is directly matched by bending to the anatomy of the bone 11 in the region destined for the use of the outrigger plate 15.

Both the main plate 13 and the outrigger plate 15 shaped to the bone 11 are fixed to the bone 11 by means of bone screws 19 which are received in bores of the main plate 13 or of the outrigger 15.

The outrigger plate 15 made, for example, from titanium, is made in one piece with two elongate, wire-like connection elements 17 which are guided in each case through a passage 27 formed in the main plate 13 and extending approximately parallel to the main plate plane. The free ends of the connection elements 17 are connected to one another by being twisted together, whereby an accidental pulling out of the connection elements 17 from the main plate 13 is avoided and a maximum spacing between the main plate 13 and the outrigger plate 15 is predetermined.

Not only the outrigger plate 15, but also the connection elements 17 can be brought into the respectively desired shape by bending, whereby the spatial structure of the implant required for the respective fracture can always be directly realised.

FIG. 2 shows an embodiment of an implant in accordance with the invention, in which the main plate 13 is provided with a hook-like continuation 29 with which the positioning of the main plate 13 at the bone is facilitated.

It is indicated by the double arrow in FIG. 2 that the spatial offset or spacing between the main plate 13 and the outrigger 15 can be changed prior to the final fixing of the connection elements 17 to the main plate 13 and the implant in accordance with the invention can be exactly matched in this manner to the respective bone fracture to be treated.

The main plate 15 is made in grid-shape and includes a plurality of ring sections 23 which are connected to one another by webs 21 whose length is smaller than the diameter of the ring sections 23. Each ring section 23 defines a passage through which a bone screw can be guided to fix the outrigger 15 to the bone to be treated.

The main plate 13 can be connected to a handle and/or to a targeting aid, such as was/were explained in the introductory part, via the two front bores 47 of the main plate 13 disposed closest to the hook 29. Such a handle or such a targeting aid is not a subject of the invention so that it is not considered in any more detail in the following.

Figure 3:
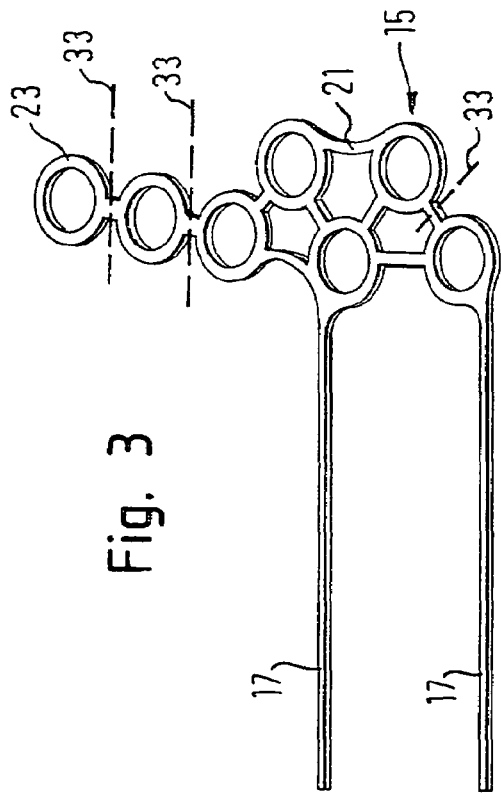
Figure 4:
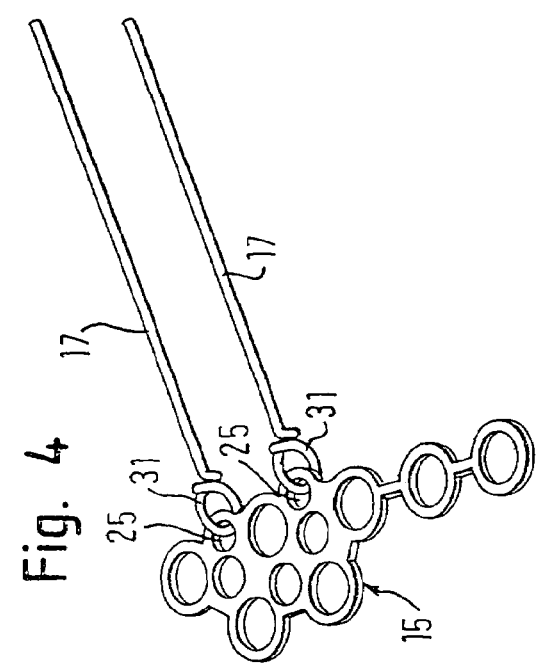

The embodiments of an outrigger plate 15 in accordance with the invention shown in FIGS. 3 and 4 differ from one another, on the one hand, in that in the variant in accordance with FIG. 4 bores are formed in a central region in a full-area material, that is the outrigger 15 is provided in the form of a perforated plate, while in the variant in accordance with FIG. 3 individual ring sections 23 are connected to one another either directly or via webs 21, whereby a continuous grid-like or mesh-like perforated structure is obtained.

On the other hand, these two variants differ from one another by the manner of the coupling of the connection elements to the outrigger 15. In the variant in accordance with FIG. 4, the connection elements 17 are each bent at their one free end to form eyelets 31 which are hooked into bores 25 of the outrigger plate 15 serving as fastening sections. In the variant in accordance with FIG. 3, the connection elements 17 are made in one piece with the outrigger plate 15.

Possible sectional lines 33 are indicated by way of example by the broken lines in FIG. 3 along which the outrigger plate 15 can be cut to the respectively required shape by taking away one or more ring sections 23.

Figure 5C:
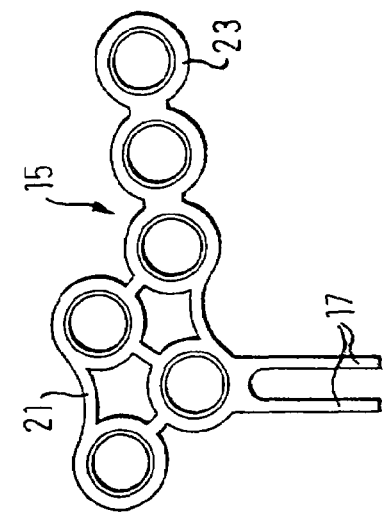
Figure 5B:
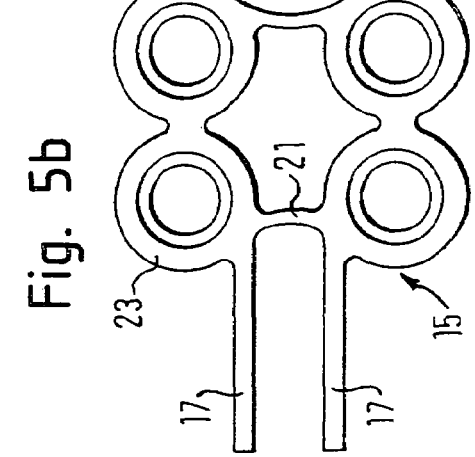
Figure 5A:
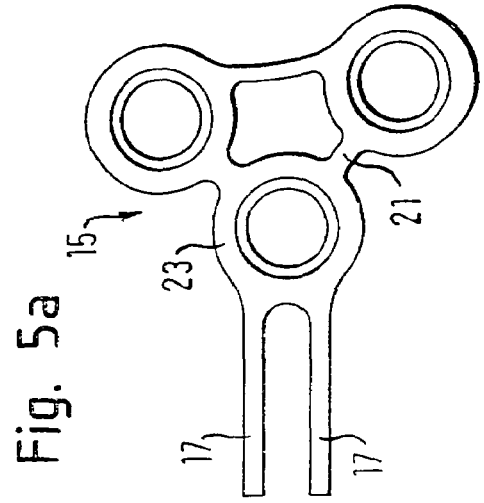

FIGS. 5a-5c show by way of example how different shapes and sizes of the outrigger plate 15 can be realized by a different number of ring elements 23 and a different manner of connection of the ring sections 23 to form a continuous am plate 15.

As in the variant in accordance with FIG. 3, the connection elements 17 in the examples of FIGS. 5a-5c are connected in one piece to the outrigger plate 15, with either both connection elements 17 starting from the same ring section 23 (cf. FIG. 5a) or being able to be connected to different ring sections 23 (cf. FIGS. 5b and 5c).

As FIG. 6 shows with reference to four examples, the coupling of the connection elements 17, formed here in each case as flexible wire, to the main plate 13 can take place (from left to right) (i) by twisting together the free ends of two connection elements 17 pushed through the main plate 13 (cf. also FIG. 1); (ii) by bending over the free ends of the connection elements 17 projecting out of the main plate 13 in the plane of the main plate 13; (iii) by guiding only a single connection element 17 through a passage formed in the main plate 13 in the one direction and by guiding back this connection element 17 through a further passage formed in the main plate 13 in the other direction; or (iv) by bending over the free ends of the connection elements 17 projecting out of the main plate 13 perpendicular to the plane of the main plate 13.

It is common to all variants of FIG. 6 shown that an accidental pulling out of the connection elements 17 from the main plate 13, and thus a release of the connection between the main plate 13 and the outrigger plate 15 (not shown in FIG. 6), is avoided.

The connection of the main plate 13 to the outrigger plate 15 via the connection elements 17 can take place prior to or during the operation. By a corresponding selection of the length of the connection elements 17, the spatial offset between the main plate 13 and the outrigger plate 15 can be individually matched to the bone fracture to be treated in each case.

FIGS. 7a-7d show further examples for the coupling of the connection elements 17 to the main plate 13.

In accordance with FIGS. 7a and 7b, the main plate 13 can be provided with channels 35 which expand at the base side and thus form an under-cut into which correspondingly shaped, for example spherically expanded, free ends 37 of the connection elements 17 can be inserted in a manner secure against pulling out by pushing in from the side (FIG. 7a) or by clipping in (FIG. 7b). In these two variants, the possibility exists in an advantageous manner of a displaceability of the outrigger plate 15 relative to the main plate 13 perpendicular to the elongate extent of the connection elements 17.

In the variant in accordance with FIG. 7c, the free ends of the connection elements 17 are provided with fastening pins 39 which can be latched to the main plate 13 at correspondingly formed cut-outs thereof.

In the variant in accordance with FIG. 7d, the free ends 41 of the connection elements 17 are made in hook shape and are hooked into the main plate 13 at correspondingly formed cut-outs serving as a fastening section in each case.

As FIGS. 7e and 7f show, the main plate 13 can additionally be provided with leadthroughs 43 through which the suturing needles or suturing material can be led. If such leadthroughs extend obliquely from the upper surface into a side surface of the main plate 13, suture material can be pulled in, e.g. by means of a round needle, even with a main plate fixed to the bone.

FIGS. 8a, 8b and 8c show different views of a preferred embodiment of a main plate 13 in accordance with the invention.

The main plate 13 can be used in conjunction with outrigger plates and connection elements which will be looked at in more detail in the following. Alternatively, the main plate 13 can, however, also be used alone as a bone plate without an outrigger.

As in particular the plan view in FIG. 8a shows, the main plate 13 has a relatively narrow section 115 which extends approximately over two thirds of its length and which is adjoined by a widened head section 117 which forms the further third of the plate length. A comparatively short end section 119 adjoins the other end of the narrow section 115 and tapers constantly to approximately half the width of the narrow section 115.

It can in particular be seen from the section A-A in FIG. 8a that the main plate 13 is not planar, but is slightly curved in the direction of its longitudinal extent such that a gently swung wave-like extent is provided. Starting approximately from the plate centre, the main plate 13 extends rearwardly obliquely upwardly at a relatively low angle of inclination amounting to a few degrees, with the plate thickness being approximately constant up to a rear chamfer 121 at the short end section 119 and in particular lying in the range from approximately 4 to 6 mm. The plate thickness right at the end of the chamfered end section 119 amounts to less than half the thickness in the narrow section 115.

Again starting approximately from the plate centre, the main plate 13 likewise extends forwardly obliquely upwardly at a relatively low angle such that the head section 117 is raised with respect to the plate centre still belonging to the narrow section 115, with, however—unlike in the rear region—the head section 117 running out approximately parallel to the centre part of the main plate 13. The head section 117 is provided with a chamfer 123 at the front end such that the head section 117 runs out in wedge shape precisely like the plate end.

The transitions between the individual sections of the plate 13 are flowing, i.e. the plate 13 has a relatively gently curved outer contour without edges with respect to its longitudinal extent.

As can in particular be seen from the plan view in FIG. 8a, the plate 13 is provided with a plurality of passages in the form of bores. A total of eight bores 125 with relatively large diameters serve to receive fastening elements in the form of bone screws. The large bores 125 are each provided with an internal thread. Six large bores 125 are arranged distributed in a sequential row, spaced apart substantially the same, along the central plane 127 of the plate 13 over the narrow section 115 up to and into the transition region to the head section 117.

The axes of these large bores 125 extend at an inclination with respect to the centre plane 127 and/or with respect to a normal on a reference surface F of the plate 13. This also applies to the two large bores 125 in the head section 117 which are arranged lying diametrically opposite one another symmetrically on both sides of the central plane 127.

The main plate 13 is furthermore provided with three further bores 129, 131 of—seen relatively—medium diameter size. The two bores 129 disposed symmetrically to the centre plane 127 at the front end of the head section 117 in the region of the chamfer 123 serve to couple the plate 13 to a handle and/or to a targeting aid such as has already been described in the introductory part. This is not looked at in any detail at this point.

Furthermore, the plate 13 is provided with three small bores 133 which lie on the centre plane 127 and of which one is disposed on the rear chamfer 121, one on the front chamfer 123 and one approximately between the large bores 125 formed in the head section 117 on the other side of the medium sized bore 131.

Marginal bores 135, 137 formed in the marginal region on the head section 117 and transverse bores 139 extending perpendicular to the centre plane 127 will be considered in more detail at another point.

The bore 125 made as a threaded bore can be used in interaction with an adjacent bore 133 for the intermittent fastening of a handle (not shown). The bores 133, 135, 137 can be used as fastening aids for pins or for threads which support soft tissues such as muscle ends or tendons. Such threads of bioabsorbable material are used when the soft tissues can anchor themselves sufficiently at a later time.

Four respective depression-like recesses 141 are formed on each side in the marginal region of the plate 13 between the large bores 125 arranged along the narrow sections 115.

As in particular the section A-A in FIG. 89a and the different sectional views in FIG. 8b show, the large bores 125 are made in step shape. A large part region of the bores 125 starting from the upper plate side respectively has a larger diameter and extends over a larger axial length than a small part region of the bores 125 opening at the lower plate side. The internal thread is respectively formed at the larger upper part region of the bores 125.

The sections B-B to H-H of the individual large bores 125 (Nos. 1 to 8) and the section A-A in FIG. 8b show that, with the exception of bores No. 3 (section C-C) and No. 4 (section D-D), the centre axes of the bores 125 extend in inclined form both with respect to a normal on the reference surface F (cf. section A-A in FIG. 8b) and with respect to the centre plane 127 of the plate 13. The centre axes of the bores 125 with the Nos. 5 to 8 are inclined by approximately 4° with respect to the centre plane 127, while this angle of inclination is somewhat lower in the bores 125 with the Nos. 1 and 2 formed in the head section 117 and preferably amounts to approximately 3.5°.

The centre axes of the bores 125 with the No. 3 (section C-C) and No. 4 (section D-D) lie in the centre plane 127, but are inclined with respect to the mentioned normal on the reference surface F.

FIG. 8c in particular shows the design of the marginal bores 135, 137 and of the transverse bores 139.

As can be seen from the sections A-A and B-B in FIG. 8c, the marginal bores 135 formed in the rear region of the head section 117 (section B-B) have a greater inclination with respect to the normal on the reference surface F than the marginal bores 137 formed in the front region of the head section 117 (section A-A).

The transverse bores 139 each extend perpendicular to the centre plane 127 of the plate 13 and have a comparatively small inner diameter which expands in each case towards the opening at the narrow sides of the plate 13, as is shown in particular by the details E and F in FIG. 8c. The narrow sides of the plate 113 extend obliquely to the longitudinal axis of the transverse bores 139 in the region of the openings.

While the transverse bores 139 serve to link one or more outriggers by means of connection elements, provided in particular in the form of wires, the marginal bores 135, 137 and the bore 133 formed in the region of the front chamber 123 for the pulling through of suture material are in particular provided using curved needles.

Not only the transverse bores 139, but also the obliquely extending marginal bores 135, 137 permit a guiding through of connection wires, when the main plate 13 contacts the bone, whereby the handling of the implant is substantially improved overall.

FIG. 9 shows a preferred embodiment of an outrigger 15 also termed an outrigger plate in the following. The outrigger 15 comprises a coherent perforated plate section 153 in which differently sized bores are formed seemingly unordered, as well as a ring row section 155 of three rings sections which are arranged sequentially in a straight line, are connected to one another by webs 157 and each bound a bore.

The outer contour of the outrigger 15 follows the boundaries of the bores such that the spacing of the plate edge to the next disposed bore or to an opposite region of the plate edge is smaller substantially everywhere than the diameter of the smallest type of bores, i.e. the outrigger 15 is so-to-day bounded by a relatively small, wave-shaped peripheral material strip.

In the embodiment shown, the outrigger 15 includes three types of bores: large bores with which the ring row section 155 is exclusively provide have a diameter of approximately 5 mm, whereas the medium sized bores have a diameter of approximately 4 mm and the small bores 159 have a diameter of approximately 2.5 mm.

As can in particular be seen from the section A-A in FIG. 9, the outrigger plate 15 is planar unlike the main plate 13 (cf. FIGS. 8a-8c). The outrigger plate 15 is substantially thinner than the main plate 13. The thickness of the outrigger plate 15 preferably amounts to approximately 1 to 2 mm, I particular to approximately 1.2 mm.

Furthermore, the base area of the outrigger plate 15 is smaller than that of the main plate 13. While the outrigger plate 15 preferably has a maximum width in the range from 15 to 20 mm, preferably approximately 17.2 mm, and a maximum length in the range from 50 to 55 mm, preferably approximately 52.1 mm, the maximum width in the main plate 13 preferably amounts to 22 to 27 mm, preferably approximately 24.4 mm, and the maximum length to 90 to 95 mm, preferably approximately 93 mm.

FIG. 10 shows different views of a cerclage wire serving as a connection element 17.

The wire 17 is bent into a U shape which is bent at right angles in the region of the U base 161, with an again U-shaped dent being provided in the central region of the bent over U base 161.

The spacing between the two U limbs 163 of the wire 17 corresponds to the spacing of the two small bores 159 in the outrigger plate 15 (cf. FIG. 9). The prefabricated wire 17 can hereby be pushed through the two bores 159 without problem and be aligned relative to the outrigger plate 15 such that the two U limbs 163 extend parallel to the plane of the outrigger plate 15, without the U base 161 extending beyond the large bore of the outrigger plate 15 located between the two small bores 159.

The U limbs 163 of the wire 17 projecting in this manner from the outrigger plate 15 coupled to the wire 17 can subsequently be deformed in the respectively required manner and be connected to the main plate 13 in that its free ends are pushed through the transverse bores 139 likewise having the corresponding spacing and are latched to the opposite side of the main plate 13, for example by bending over or twisting together, such that the wire 17, and thus the outrigger 15, is connected to the main plate 13 secure against being pulled out.

The outrigger 15 and the wire 17, which are made as separate components, can be connected to one another so firmly, e.g. by welding, prior to the operation, and in particular as part of the manufacture, that they can be handled as one unit during the operation.

In the aforesaid embodiment, in which the main plate 13 only has one pair of transverse bores 139, only one single outrigger 15 is preferably connected to the main plate 13 via a prefabricated U-shaped wire 17, e.g. in accordance with FIG. 10. The main plate 13 and the outrigger 15 are therefore only connected to one another at one side by means of the wire 17, i.e. the wire 17 only extends—starting from one side of the main plate 13—to the outrigger plate 15.

The outrigger plate 15 consisting in particular of titanium is deformable without tools during the operation due to its low thickness such that the surgeon can put the outrigger plate 15, which is planar in the starting state, into the respectively desired shape using only his hands.

The outrigger plate 15, which in the embodiment of FIG. 9 comprises the perforated plate section 153 comprising so-to-say a "heap" of bores and the ring row section 155, which is in contrast small and elongate, has been selected with respect to its basic shape such that it is sufficiently large for all common fractures of the tuberculum minus and can be matched to the respective bone fracture to be treated by cutting to shape with an appropriate tool.

REFERENCE NUMERAL LIST 11 bone
13 main plate
15 outrigger
17 connection element
19 fastening element, bone screw
21 web
23 ring section
25 fastening section, bore
27 passage
29 continuation
31 eyelet
33 sectional line
35 channel
37 extension
39 fastening pin
41 hook-shaped end
43 leadthrough
45 fastening section, cut-out
47 bore for handle or targeting aid
115 narrow section
117 head section 119 end section
121 rear chamfer
123 front chamfer
125 large bore
127 centre plane
129 bore
131 bore
133 bore
135 marginal bore
137 marginal bore
139 transverse bore
141 recess
153 perforated plate section
155 ring row section
157 web
159 small bore of the outrigger
161 U base
163 U limb
F reference surface of the main plate

The invention claimed is:

1. An implant for treatment of bone fractures, the implant comprising a main plate adapted to be fixed to a bone and a plate-shaped outrigger element adapted to be fixed to the bone, the main plate having a first side and a second side, wherein, in an assembled state of the implant, the plate-shaped outrigger element is arranged offset from the main plate and the second side of the main plate is positioned further from the plate-shaped outrigger element than the first side of the main plate, the implant further comprising a U-shape flexible connection element having a pair of U limbs extending outwardly from a U base, each of the pair of U limbs having a terminal end, wherein the U-shape flexible connection element connects the main plate and the plate-shaped outrigger element to treat a bone fracture, the U-shape flexible connection element extending less than entirely around a periphery of the bone in the assembled state of the implant; and wherein the main plate has at least one pair of first passages through which the U limbs of the U-shape flexible connection element are guidable, wherein, in the assembled state of the implant, the U base of the U-shape flexible connection element is positioned outside of an aperture of the plate-shaped outrigger element, and the said terminal end of one of the pair of U limbs passing through one of the pair of first passages in the main plate from the first side of the main plate to the second side of the main plate and said terminal end of another one of the pair of U limbs passing through another one of the pair of first passages in the main plate from the first side of the main plate to the second side of the main plate, wherein, in the assembled state of the implant, the terminal ends of both of the pair of U limbs are positioned adjacent to the second side of the main plate.

2. The implant in accordance with claim 1, wherein the U-shape flexible connection element has an elongate U-shape.

3. The implant in accordance with claim 1, wherein the U-shape flexible connection element is one of a wire and a thread.

4. The implant in accordance with claim 1, wherein the U-shape flexible connection element is coupled to at least one of the main plate and the plate-shaped outrigger element by at least one of tying, hooking, and latching.

5. The implant in accordance with claim 1, wherein the plate-shaped outrigger element has a plurality of passages for the reception of fastening elements.

6. The implant of claim 5, wherein the passages are adapted to receive bone screws.

7. The implant in accordance with claim 1, wherein the plate-shaped outrigger element is provided with at least five passages to receive fastening elements.

8. The implant of claim 1, wherein the U limbs of the U-shape flexible connection element are received through the at least one pair of second passages in the plate-shaped outrigger element and are led through the at least one pair of first passages in the main plate, the U limbs of the U-shape flexible connection element being connected to each other at free ends remote from the plate-shaped outrigger element.

9. The implant of claim 8, wherein the free ends are at least one of knotted and twisted together.

10. The implant in accordance with claim 1, wherein the plate-shaped outrigger element is flexible.

11. The implant in accordance with claim 1, wherein the plate-shaped outrigger element is formed as a perforated plate.

12. The implant in accordance with claim 1, wherein the plate-shaped outrigger element is made in at least one of a mesh-like and a grid-like shape.

13. The implant in accordance with claim 1, wherein the plate-shaped outrigger element includes a plurality of ring sections connected to one another directly or by webs and each bounding a passage.

14. The implant in accordance with claim 1, wherein the plate-shaped outrigger element and the U-shape flexible connection element are unreleasably connected to one another.

15. The implant in accordance with claim 1, wherein the spatial offset between the main plate and the plate-shaped outrigger element corresponds to a length of the U limbs of the U-shape flexible connection element.

16. The implant in accordance with claim 1, wherein the U-shape flexible connection element can be fixed at different positions relative to at least one of the main plate and the plate-shaped outrigger element.

17. The implant in accordance with claim 1, wherein at least one of the main plate and the plate-shaped outrigger element have at least one of a hook-like and claw-like configuration.

18. The implant in accordance with claim 1, wherein the plate-shaped outrigger element has smaller thickness than the main plate.

19. The implant in accordance with claim 18, wherein the thickness of the plate-shaped outrigger element is less than half the thickness of the main plate.

20. The implant in accordance with claim 1, wherein the plate-shaped outrigger element is deformable without tools during an operation.

21. The implant in accordance with claim 1, wherein the plate-shaped outrigger element includes a bioabsorbable material.

22. The implant in accordance with claim 21, wherein the bioabsorbable material is plastically deformable at temperatures between 50 and 90° C.

23. The implant in accordance with claim 21, wherein the bioabsorbable material comprises a polymer.

24. The implant in accordance with claim 1, wherein the plate-shaped outrigger element and the U-shape flexible connection element are monolithic.

25. An implant for the treatment of bone fractures, the implant comprising a main plate adapted to be fixed to a bone and a plate-shaped outrigger element adapted to be fixed to the bone, the main plate having a first side and a second side, wherein, in an assembled state of the implant, the plate-shaped outrigger element is arranged offset from the main plate and the second side of the main plate is positioned further from the plate-shaped outrigger element than the first side of the main plate, the implant further comprising a U-shape flexible connection element having a pair of U limbs extending outwardly from a U base, each of the pair of U limbs having a terminal end, wherein the U-shape flexible connection element connects the main plate and the plate-shaped outrigger element to treat a bone fracture, the U-shape flexible connection element extending less than entirely around a periphery of the bone in the assembled state of the implant;

wherein the main plate has at least one pair of first passages through which the U limbs of the U-shape flexible connection element are guidable, wherein, in the assembled state of the implant, the U base of the U-shape flexible connection element is positioned outside of an aperture of the plate-shaped outrigger element, and the terminal end of one of the pair of U limbs passing through one of the pair of first passages in the main plate from the first side of the main plate to the second side of the main plate and the terminal end of another one of the pair of U limbs passing through another one of the pair of first passages in the main plate from the first side of the main plate to the second side of the main plate, wherein, in the assembled state of the implant, the terminal ends of both of the pair of U limbs are positioned adjacent to the second side of the main plate; and wherein the plate-shaped outrigger element has a base area substantially smaller than that of the main plate.

26. An implant for the treatment of bone fractures, the implant comprising a main plate adapted to be fixed to a bone and a plate-shaped outrigger element adapted to be fixed to the bone, the main plate having a first side and a second side, wherein, in an assembled state of the implant, the plate-shaped outrigger element is arranged offset from the main plate and the second side of the main plate is positioned further from the plate-shaped outrigger element than the first side of the main plate, the implant further comprising a U-shape flexible connection element having a pair of U limbs extending outwardly from a U base, each of the pair of U limbs having a terminal end, wherein the U-shape flexible connection element connects the main plate and the plate-shaped outrigger element to treat a bone fracture, the U-shape flexible connection element extending less than entirely around a periphery of the bone in the assembled state of the implant;

wherein the main plate has at least one pair of first passages through which the U limbs of the U-shape flexible connection element are guidable, wherein, in the assembled state of the implant, the U base of the U-shape flexible connection element is positioned outside of an aperture of the plate-shaped outrigger element, and the terminal end of one of the pair of U limbs passing through one of the pair of first passages in the main plate from the first side of the main plate to the second side of the main plate and the terminal end of another one of the pair of U limbs passing through the other one of the pair of first passages in the main plate from the first side of the main plate to the second side of the main plate, wherein, in the assembled state of the implant, the terminal ends of both of the pair of U limbs are positioned adjacent to the second side of the main plate; and wherein the plate-shaped outrigger element has a base area substantially smaller than that of the main plate.

\* \* \* \* \*